(12) United States Patent
Ho (10) Patent No.: US 10,080,654 B2
(45) Date of Patent: *Sep. 25, 2018

(54) METHODS AND APPARATUS FOR PERCUTANEOUS AORTIC VALVE REPLACEMENT

(71) Applicant: HOCOR Cardiovascular Technologies, LLC, Honolulu, HI (US)

(72) Inventor: Paul C. Ho, Honolulu, HI (US)

(73) Assignee: HOCOR Cardiovascular Technologies, LLC, Honolulu, HI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/277,807

(22) Filed: Sep. 27, 2016

(65) Prior Publication Data
US 2017/0079783 A1 Mar. 23, 2017

Related U.S. Application Data

(63) Continuation of application No. 14/154,890, filed on Jan. 14, 2014, now Pat. No. 9,480,564, which is a
(Continued)

(51) Int. Cl.
*A61F 2/24* (2006.01)
*A61B 17/12* (2006.01)
*A61B 17/00* (2006.01)

(52) U.S. Cl.
CPC ........ *A61F 2/2418* (2013.01); *A61B 17/1204* (2013.01); *A61B 17/12036* (2013.01);
(Continued)

(58) Field of Classification Search
CPC ...... A61F 2/2427; A61F 2/243; A61F 2/2433; A61F 2/2436
(Continued)

(56) References Cited

U.S. PATENT DOCUMENTS

| 3,671,979 A | 6/1972 | Spyridon |
| 4,056,854 A | 11/1977 | Boretos et al. |

(Continued)

FOREIGN PATENT DOCUMENTS

| WO | WO-0044313 A1 | 8/2000 |
| WO | WO-0047139 A1 | 8/2000 |

(Continued)

OTHER PUBLICATIONS

Andersen, et al. Transluminal implantation of artificial heart valves: description of a new expandable aortic valve and initial results with implantation by catheter technique in closed chest pigs. Eur Heart J 1992;13:704-708.
(Continued)

*Primary Examiner* — Melanie Tyson
(74) *Attorney, Agent, or Firm* — Wilson, Sonsini, Goodrich & Rosati (57) ABSTRACT

A delivery system and method for percutaneous aortic valve (PAV) replacement and apparatus used therein. A temporary aortic valve including a reversibly expandable occluding medium surrounds a central catheter mechanism. The temporary valve is positioned within the ascending aorta, just above and downstream from the coronary ostia. The occluding medium is configured such that, when fully expanded against the aortic wall, gaps are left that promote continuous coronary perfusion during the cardiac cycle. The temporary valve substitutes for the function of the native aortic valve during its replacement. The native aortic valve is next dilated, and then ablated through deployment of low profile, elongated, sequentially delivered stents. The stent(s) displace the native tissues and remain within the aortic annulus to receive and provide a structure for retaining the PAV. The PAV is delivered, positioned and deployed within the stent(s) at the aortic annulus with precision and relative ease.

23 Claims, 9 Drawing Sheets

Related U.S. Application Data continuation of application No. 12/180,223, filed on Jul. 25, 2008, now Pat. No. 8,663,319, which is a continuation-in-part of application No. 11/781,924, filed on Jul. 23, 2007, now Pat. No. 8,663,318.

(52) U.S. Cl.
CPC .. *A61B 17/12109* (2013.01); *A61B 17/12122* (2013.01); *A61B 17/12136* (2013.01); *A61F 2/2433* (2013.01); *A61B 2017/00703* (2013.01); *A61F 2250/006* (2013.01); *A61F 2250/0059* (2013.01)

(58) Field of Classification Search
USPC ........................................................ 623/2.11
See application file for complete search history.

(56) References Cited

U.S. PATENT DOCUMENTS

| | | |
|---|---|---|
| 4,705,507 A | 11/1987 | Boyles |
| 4,787,388 A | 11/1988 | Hofmann |
| 4,816,029 A | 3/1989 | Penny, III et al. |
| 4,878,495 A | 11/1989 | Grayzel |
| 5,295,960 A | 3/1994 | Aliahmad et al. |
| 5,308,323 A | 5/1994 | Sogawa et al. |
| 5,308,356 A | 5/1994 | Blackshear, Jr. et al. |
| 5,383,856 A | 1/1995 | Bersin |
| 5,403,280 A | 4/1995 | Wang |
| 5,411,552 A | 5/1995 | Andersen et al. |
| 5,458,575 A | 10/1995 | Wang |
| 5,505,702 A | 4/1996 | Arney |
| 5,645,529 A | 7/1997 | Fagan et al. |
| 5,718,684 A | 2/1998 | Gupta |
| 5,792,300 A | 8/1998 | Inderbitzen et al. |
| 5,827,321 A | 10/1998 | Roubin et al. |
| 5,910,103 A | 6/1999 | Saper et al. |
| 5,938,582 A | 8/1999 | Ciamacco, Jr. et al. |
| 6,068,611 A | 5/2000 | Loffler et al. |
| 6,117,064 A | 9/2000 | Apple et al. |
| 6,234,952 B1 | 5/2001 | Liprie |
| 6,425,916 B1 * | 7/2002 | Garrison .............. A61F 2/2418 623/1.26 |
| 6,482,228 B1 | 11/2002 | Norred |
| 6,540,734 B1 | 4/2003 | Chiu et al. |
| 6,544,224 B1 | 4/2003 | Steese-Bradley |
| 6,610,083 B2 | 8/2003 | Keller et al. |
| 6,656,714 B2 | 12/2003 | Holmes et al. |
| 6,709,440 B2 | 3/2004 | Callol et al. |
| 6,761,731 B2 | 7/2004 | Majercak |
| 6,769,434 B2 | 8/2004 | Liddicoat et al. |
| 6,835,188 B2 | 12/2004 | Samson et al. |
| 6,896,690 B1 | 5/2005 | Lambrecht et al. |
| 6,929,653 B2 | 8/2005 | Strecter |
| 6,989,027 B2 | 1/2006 | Allen et al. |
| 7,011,681 B2 | 3/2006 | Vesely |
| 7,267,686 B2 | 9/2007 | Dimatteo et al. |
| 7,329,279 B2 | 2/2008 | Haug et al. |
| 7,585,321 B2 | 9/2009 | Cribier |
| 8,579,966 B2 | 11/2013 | Seguin et al. |
| 8,663,318 B2 | 3/2014 | Ho |
| 8,663,319 B2 | 3/2014 | Ho |
| 9,480,564 B2 | 11/2016 | Ho |
| 2002/0013616 A1 | 1/2002 | Carter et al. |
| 2002/0151970 A1 | 10/2002 | Garrison et al. |
| 2003/0105517 A1 | 6/2003 | White et al. |
| 2004/0059412 A1 | 3/2004 | Lytle et al. |
| 2004/0215333 A1 | 10/2004 | Duran et al. |
| 2004/0225354 A1 | 11/2004 | Allen et al. |
| 2004/0236418 A1 * | 11/2004 | Stevens .......... A61B 17/320758 623/2.11 |
| 2005/0075718 A1 | 4/2005 | Nguyen et al. |
| 2005/0137688 A1 | 6/2005 | Salahieh et al. |
| 2005/0154344 A1 | 7/2005 | Chang |
| 2005/0171472 A1 | 8/2005 | Lutter |
| 2005/0215333 A1 | 9/2005 | Lin |
| 2005/0228402 A1 | 10/2005 | Hofmann |
| 2006/0020332 A1 | 1/2006 | Lashinski et al. |
| 2006/0025855 A1 | 2/2006 | Lashinski et al. |
| 2006/0036317 A1 | 2/2006 | Vidlund et al. |
| 2006/0052867 A1 | 3/2006 | Revuelta et al. |
| 2006/0074483 A1 | 4/2006 | Schrayer |
| 2006/0074484 A1 | 4/2006 | Huber et al. |
| 2006/0142848 A1 | 6/2006 | Gabbay |
| 2006/0247570 A1 | 11/2006 | Pokorney |
| 2006/0259137 A1 | 11/2006 | Artof et al. |
| 2007/0073387 A1 | 3/2007 | Forster et al. |
| 2007/0219630 A1 | 9/2007 | Chu |
| 2008/0125853 A1 | 5/2008 | Bailey et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0200898 A1 | 8/2008 | Lashinski |
| 2008/0269877 A1 | 10/2008 | Jenson et al. |
| 2009/0030503 A1 | 1/2009 | Ho |
| 2009/0030510 A1 | 1/2009 | Ho |
| 2009/0069886 A1 | 3/2009 | Suri et al. |
| 2014/0200658 A1 | 7/2014 | Ho |

FOREIGN PATENT DOCUMENTS

| | | |
|---|---|---|
| WO | WO-2007100410 A2 | 9/2007 |
| WO | WO-2008051554 A2 | 5/2008 |
| WO | WO-2009052838 A1 | 4/2009 |
| WO | WO-2010011736 A1 | 1/2010 |

OTHER PUBLICATIONS

Bahl, et al. Balloon aortic valvuloplasty in young adults by antegrade, transseptal approach using the Inoue balloon. Cathet Cardiovasc Diagn 1998;44(3):297-301.

Bonhoeffer, et al. Percutaneous replacement of pulmonary valve in a right-ventricle to pulmonary-artery prosthetic conduit with valve dysfunction. Lancet 2000;356:1403-1405.

Boudjemline, et al. Steps toward percutaneous aortic valve replacement. Circulation 2002;105(6):775.

Carabello. Aortic Stenosis. N Engl J Med 2002;346(9):677-682.

Cribier, et al. Percutaneous transcatheter implantation of an aortic valve prosthesis for calcific aortic stenosis: first human case description. Circulation 2002;106(24):3006-3008.

Dewey, et a; Transapical Aortic Valve Implantation: an Animal Feasibility Study. Ann Thorac Surg 2006; 82(1):110-116.

Endovascular Repair of Thoracic Aortic Disease: Gore TAG Endoprosthesis; Medscape.com. Mar. 15, 2010.

European search report dated Nov. 6, 2013 for EP Application No. 09800932.7.

Ferrari, et al. Transarterial aortic valve replacement with a self expanding stent in pigs. Heart 2004;90(11):1326-1331.

Gore Medical, Gore® Tri-Lobe Balloon Catheter Product Information [Technical Information]; retreived from the Internet: <http://goremedical.com/resources/dam/assets/AN0634-EN2.pdf>, 2009 W. L. Gore & Associates, Inc., 2 pages total.

Grube, et al. Percutaneous aortic valve replacement for severe aortic stenosis in high-risk patients using the second- and current third-generation self-expanding CoreValve prosthesis. J Am Coll Cardiol 2007;50:69-76.

Hanzel, et al. Retrograde Percutaneous Aortic Valve Implantation for Critical Aortic Stenosis. Catheter Cardiovasc. Interv. 2005, 64(3)' 322-326.

Ho. Percutaneous aortic valve replacement: a novel design of the delivery and deployment system. Minim Invasive Ther Allied Technol. 2008;17(3):190-194.

International search report and written opinion dated Sep. 23, 2009 for PCT/US2009/051389.

Lichtenstein, et al. Transapical transcatheter aortic valve implantation in humans: initial clinical experience. Circulation 2006;114(6):591-596.

Notice of allowance dated Jun. 27, 2016 for U.S. Appl. No. 14/154,890.

(56) References Cited

OTHER PUBLICATIONS

Notice of allowance dated Nov. 27, 2013 for U.S. Appl. No. 11/781,924.
Notice of allowance dated Dec. 19, 2013 for U.S. Appl. No. 12/180,223.
Office action dated Feb. 4, 2011 for U.S. Appl. No. 11/781,924.
Office action dated Mar. 26, 2010 for U.S. Appl. No. 11/781,924.
Office action dated Mar. 28, 2011 for U.S. Appl. No. 12/180,223.
Office action dated Jun. 24, 2015 for U.S. Appl. No. 14/154,890.
Office action dated Aug. 19, 2015 for U.S. Appl. No. 14/155,060.
Office action dated Sep. 30, 2010 for U.S. Appl. No. 11/781,924.
Office action dated Oct. 8, 2015 for U.S. Appl. No. 14/154,890.
Office action dated Oct. 9, 2013 for U.S. Appl. No. 12/180,223.
Office action dated Oct. 29, 2010 for U.S. Appl. No. 12/180,223.
Office action dated Nov. 10, 2016 for U.S. Appl. No. 14/155,060.
Office action dated Dec. 8, 2015 for U.S. Appl. No. 14/155,060.
Office action dated Dec. 21, 2015 for U.S. Appl. No. 14/154,890.
Salizzoni, et al. Transapical off-pump removal of the native aortic valve: A proof-of-concept animal study. J Thorac Cardiovasc Surg, Aug. 2009;138:468-473.
Vandenberghe, et al. In Vitro Testing of a Temperary Catherter-Based Aortic 'Parachute' Valve. ASAIO Journal 2008, v. 54, 574-577.
Velling, et al Colonic Stent Placement Facilitated by Percutaneous Cecostomy and Antegrade Enema. American Journal of Roentgenology 2000; 175:119-120.
Webb, et al. Percutaneous aortic valve implantation retrograde from the femoral artery. Circulation 2006;113:842-850.
Zoghbi, et al. Recommendations for evaluation of the severity of native valvular regurgitation with two-dimensional and Doppler echocardiography. J Am Soc Echocardiogr 2003;16:777-802.

\* cited by examiner

METHODS AND APPARATUS FOR PERCUTANEOUS AORTIC VALVE REPLACEMENT

CROSS-REFERENCE TO RELATED APPLICATIONS

This application is a continuation of U.S. patent application Ser. No. 14/154,890, filed Jan. 14, 2014 and entitled "Methods and Apparatus for Percutaneous Aortic Valve Replacement," now U.S. Pat. No. 9,480,564, which is a continuation of U.S. patent application Ser. No. 12/180,223, filed Jul. 25, 2008 and entitled "Methods and Apparatus for Percutaneous Aortic Valve Replacement," now U.S. Pat. No. 8,663,319, which is a continuation-in-part of U.S. patent application Ser. No. 11/781,924, filed Jul. 23, 2007 and entitled "Method and Apparatus for Percutaneous Aortic Valve Replacement," now U.S. Pat. No. 8,663,318, the entire disclosures of which are incorporated herein by reference in their entirety and to which applications priority is claimed under 35 USC § 120.

This application is related to co-pending and co-assigned U.S. patent application Ser. No. 13/227,276, filed Sep. 7, 2011 and entitled "Method and System for Balloon Counterpulsation During Aortic Valve Replacement," the contents of which are incorporated herein by reference.

FIELD OF THE INVENTION

The technical field of this disclosure is medical procedures and devices. More specifically, this disclosure describes a system for the percutaneous delivery, deployment and assembly of aortic replacement valve components facilitated by a temporary aortic valve.

BACKGROUND OF THE INVENTION

The current standard of care for patients with significant aortic valve disease is still surgical aortic valve replacement. As the treatment of many cardiovascular diseases has become minimally invasive and catheter-based, endovascular techniques and equipment has led to the development of percutaneous aortic valve (PAV) replacement as a potential clinical reality. PAV replacement is currently an investigational procedure.

The notion of PAV replacement was first introduced in 1992 by Andersen et al. in a swine model [Andersen H R et al., *Eur Heart J* 1992; 13:704-7081]. The first human implantation of a percutaneous valved-stent was performed in the pulmonic position as reported by Bonhoeffer et al. in 2000 [Bonhoeffer P, et al., *Lancet* 2000; 356:1403-1405]. The first human implantation of a PAV was described in 2002 using a valved-stent design by Cribier et al. via the antegrade/inter-atrial septal puncture approach [Cribier A, et al., *Circulation* 2002; 106(24):3006-3008]. Other techniques such as retrograde and transapical approaches of delivery and deployment of the PAV were later introduced [Webb J G, et al., *Circulation* 2006; 113:842-850; Lichtenstein S V, et al., *Circulation* 2006; 114(6):591-596].

Notwithstanding early inroads, the percutaneous approach to aortic valve replacement is challenged by multiple key issues that currently frustrate the success of the procedure. It remains an investigational procedure rather than mainstay therapy for many patients who may be benefited. Significant obstacles include accurate placement of the PAV at the aortic annulus to avoid damaging important adjacent structures and vascular complications resulting from the large size delivery system.

In the PAV replacement procedure, most of the cardiac complications occur at the required precise placement of the PAV during implantation. Due to the aortic valve's close proximity to the coronary ostia on one side, and the mitral valve on the other, misalignment of the PAV can cause serious compromise of coronary or mitral valve function [Boudjemline Y, et al., *Circulation* 2002; 105(6):775; Ferrari M, et al., *Heart* 2004; 90(11):1326-1331]. The significant hemodynamic forces encountered at the left ventricular outflow tract to the ascending aorta, together with the anatomic structures comprising the diseased native valve, add to the difficulty of precise placement of the PAV and the risk of device embolization.

Percutaneous aortic valve replacement bears analogy to percutaneous coronary intervention (PCI) of complicated left main stenosis in the high risk nature and potential for patient instability. In patients with complex coronary disease and high risk factors, the operator has the option to support the hemodynamics by inserting an intra-aortic balloon pump (IABP) [Mishra S et al., *Am J Cardiol* 2006; 98(5):608-612]. Current investigational systems do not possess similar capabilities for prophylactic protection and hemodynamic support for those performing PAV procedures.

Vascular complications also result from the large size of currently available PAV delivery systems. The large French size catheter systems currently in use to deliver replacement valves percutaneously have the potential to cause significant injuries. [Boudjemline Y, et al., *Circulation* 2002; 105(6):775; Ferrari M. et al., *Heart* 2004; 90(11):1326-1331; Grube E, et al., *J Am Coll Cardiol* 2007; 50:69-76; Hanzel G S, et al., *Catheter Cardiovasc Interv* 2005; 64(3):322-326]. The diameter of the PAV delivery catheter system must be reduced in order for the procedure to become safe and routine.

Objects of the present invention include providing a PAV delivery and deployment system that demonstrates structural integrity and that includes specific features to optimize precise PAV placement and deployment while maintaining patient stability. Precise PAV placement and deployment can be facilitated by removing anatomic structures that can hinder or interfere with precise PAV placement, and by minimizing the hemodynamic forces on the devices encountered by the surgeon during the PAV replacement procedure. Maintaining patient stability during the replacement procedure can be facilitated by providing a substitute valve that promotes coronary perfusion while moderating stresses (aortic insufficiency and aortic stenosis) experienced by cardiac muscle prior to the PAV becoming operational.

Further objects of the present invention include providing a PAV delivery system demonstrating a significantly reduced French size to minimize the risk of vascular injuries consequent to the PAV delivery procedure.

SUMMARY OF THE INVENTION

These and other problems are solved by the subject invention, a novel method for percutaneous aortic valve replacement that employs a novel temporary aortic valve (TAV), and the miniaturization and sequential delivery and deployment of the replacement valve components.

Salient features of the PAV delivery and deployment system of the present invention are the capability to (1) achieve an adequately stable physiologic and anatomic environment for device positioning and deployment, and (2) maintain sustainable hemodynamic conditions allowing for the completion of the procedure without undue patient instability. To achieve a stable environment for both the PAV implantation and patient safety, a temporary "aortic valve" is introduced into the ascending aorta. To simplify the local anatomy and allow for a relatively unobstructed PAV placement, pre-dilation and ablation of the native aortic valve precedes PAV delivery and deployment.

The novel apparatus of the subject invention comprises a temporary aortic valve (TAV) having a plurality of inflatable balloon means. The balloon means are contiguously arranged around a central catheter. The TAV and its central catheter, with balloons deflated, is advanced over a guide wire to a position within the ascending aorta just above the Sinus of Valsalva and coronary ostia.

Once inflated, the TAV functions as a valve allowing limited blood flow in a forward direction, up through the coronary arteries and ascending aorta during systole. During diastole, the TAV functions to limit backflow into the left ventricle while still allowing continued perfusion in the coronary arteries.

The TAV promotes patient stability during the PAV replacement procedure in at least two ways. First, use of the TAV promotes continuous coronary perfusion during native valve ablation and replacement. Second, use of the TAV in place of the ablated native stenotic aortic valve minimizes the stress encountered by the cardiac muscle due to partial alleviation of the transvalvular pressure gradient.

With the TAV inflated in position, mathematical calculations demonstrate that the effective moderate range aortic stenosis and insufficiency at the TAV, generated by channels remaining with the balloons contacting the aortic wall, should be well tolerated by the subject when the native aortic valve is initially ablated. [Ho P C., *Minimally Invasive Therapy* 2007 [Epub ahead of print]. This feature can allow the subject to sustain relative stable hemodynamics and quiescent flow conditions for the complete expansion of the aortic annulus (pre-dilatation and pre-stenting), and subsequent accurate placement of the PAV.

In addition, the contiguous design of the TAV with central catheter provides a reliable vehicle demonstrating structural integrity for the delivery and deployment of the PAV device and related procedural tools, allowing the PAV components to be miniaturized and delivered, sequentially through a narrow central catheter having a reduced diameter.

The novel method of the subject invention involves pre-dilation of the native aortic valve followed by ablation (displacement from the main channel) of the native valve by pressing and compressing the native valve leaflets against the walls of the aortic annulus, all with the TAV in place.

Based on the TAV design, significant reduction in the diameter (French size) of the delivery catheter is possible, to the 8-12 Fr. range. The novel method of the subject invention further involves the use of sequentially delivered, low profile stent(s) and other PAV components that dilate, ablate and form the replacement aortic valve (PAV). The low profile stent components, fabricated from high strength composite materials can, in addition, be delivered in elongated form such that, once in position, the components are expanded against the aortic annulus and foreshorten.

More particularly, the method comprises the steps of crossing the native aortic valve with a guide wire in conventional retrograde fashion; advancing the TAV with central catheter over the guide wire within the ascending aorta; positioning and the TAV within the ascending aorta just above the Sinus of Valsalva where it is inflated; advancing a pre-dilation balloon through the TAV central catheter and over the guide wire to a position across the native aortic valve; inflating the pre-dilation balloon to dilate the diseased native valve and then withdrawing the pre-dilation balloon; advancing one or more low profile ablation stent(s) with stent catheter in elongated form into position across the native valve; deploying while foreshortening the ablation stent(s) (if more than one, one inside the other) to ablate the native valve leaflets against the walls of the aortic annulus and maintain the annulus well expanded; withdrawing the stent catheter; advancing a low profile percutaneous bioprosthetic aortic valve (PAV) with deployment catheter into position within the aortic annulus; deploying the PAV within the low profile stent(s); and then withdrawing the PAV deployment catheter and any remaining deployment tools; and finally deflating and withdrawing the TAV and guide wire.

Although pre-dilation of the diseased native valve will normally follow deployment of the TAV, pre-dilation can also proceed the step of TAV deployment when, for example, stenosis from the diseased aortic valve is particularly severe.

The TAV is intended to temporarily substitute for the function of the native aortic valve during its replacement. By engineering design, the hemodynamics supported by the TAV afford the operator invaluable time to favorably modify the aortic annulus' anatomy before PAV delivery and deployment and allows for precise placement of the PAV. Unlike most existing PAV replacement procedures, the subject PAV replacement procedure supported by the TAV is not a one-step, hit-or-miss deployment process performed under unfavorable flow and hemodynamic conditions.

The combination of the TAV hemodynamic support and the reduction in catheter size of the overall PAV delivery system can finally bring PAV replacement to mainstay therapy as a stand-alone, routine, entirely percutaneous and cath lab-based procedure.

Further objects and advantages of this invention will become apparent from consideration of the drawings and ensuing description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE PRESENTLY PREFERRED EMBODIMENTS

Temporary Aortic Valve

Figures 1, 2:
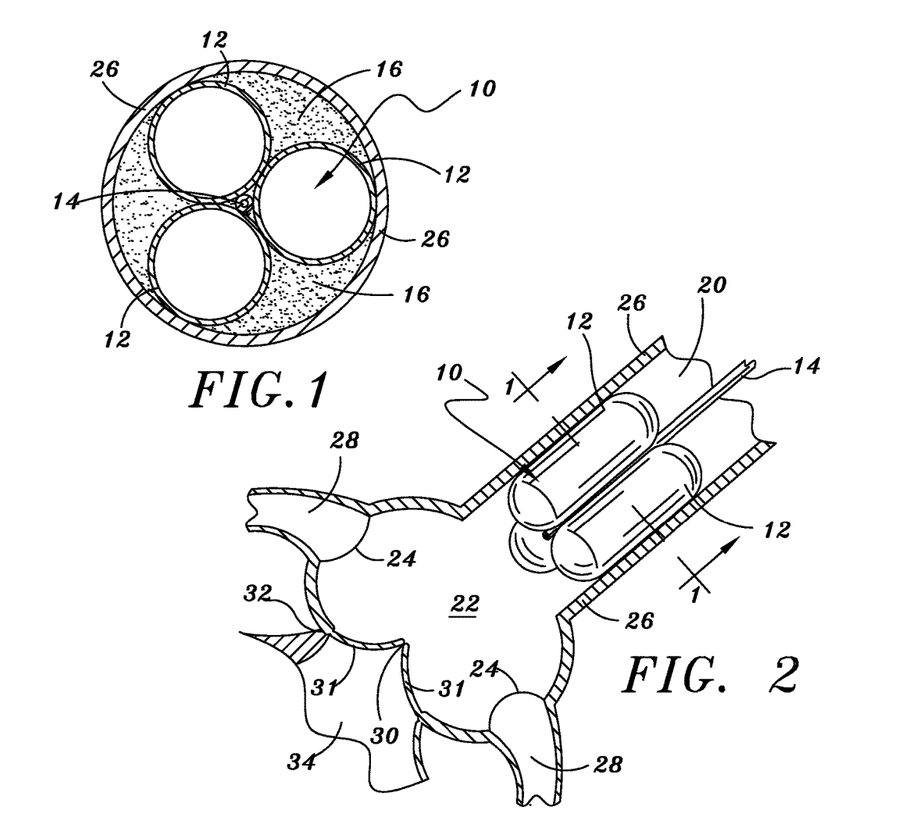
FIG. 1 illustrates in cross-sectional view, taken along line 1-1 of FIG. 2, the temporary aortic valve (TAV) of the present invention. The TAV is shown fully deployed, inflated against the inside wall of the ascending aorta, leaving gaps (shaded area) for continuous blood flow.
FIG. 2 shows in longitudinal (axial) view the TAV system of the present invention deployed within the ascending aorta, positioned just above (downstream from) the Sinus of Valsalva and coronary ostia.

Illustrated in FIG. 1 in cross section and FIG. 2 in side view is the temporary aortic valve (TAV) 10 of the present invention. According to the preferred embodiment shown, TAV 10 is comprised of three elongated supporting-balloons 12 of equal shape and size, contiguously arranged in parallel around a central guiding-catheter mechanism 14.

TAV 10 is placed within the ascending aorta 20 by means of catheter 14, and then inflated. FIG. 2 depicts TAV 10 deployed to a position within ascending aortic 20 just above (downstream from) the Sinus of Valsalva 22 and the coronary ostia 24. Once in position, supporting balloons 12 are inflated such that TAV 10 is lodged firmly against the inside walls 26 of ascending aorta 20.

Central catheter 14 sitting within the multi-balloon TAV 10 can be fashioned to the necessary French-size to accommodate the PAV device and related tools. When the PAV device and related tools are miniaturized (as described below), the French-size of catheter 14 can likewise be reduced. The contiguous design of TAV 10 and central catheter 14 provide added mechanical stability and support for the delivery and deployment the PAV device as well as the tools (described below) used to prepare the aortic annulus for PAV implantation.

The gaps 16 shown shaded in FIG. 1, between the supporting balloons 12 and aortic wall 26, allow limited blood flow, creating temporary effective aortic insufficiency (AI) and aortic stenosis (AS). As explained below, the temporary AI (during diastole) and AS (during systole) thus created are deliberately designed to serve important functions during the percutaneous aortic valve (PAV) implant procedure.

Figure 3:
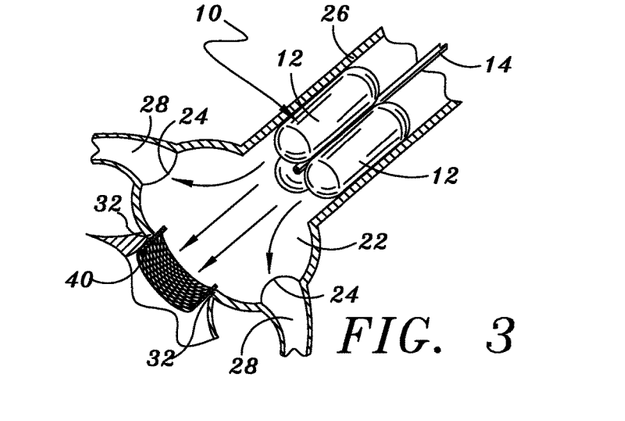
FIG. 3 illustrates the fluid dynamics of the TAV system of the present invention positioned within the ascending aorta as shown in FIG. 2, during diastole, with the native aortic valve ablated and ablation stent in place.

FIG. 3 shows the fluid dynamics of the method of the present invention, with TAV 10 deployed in position, during diastole. The arrows depict limited retrograde blood flow from TAV 10 back into the left ventricle 34 (shown in FIG. 2) while permitting coronary perfusion through ostia 24. Accordingly, TAV 10 limits the amount of AI into left ventricle 34 while allowing for continued diastolic filling of the coronary arteries 28.

Figure 4:
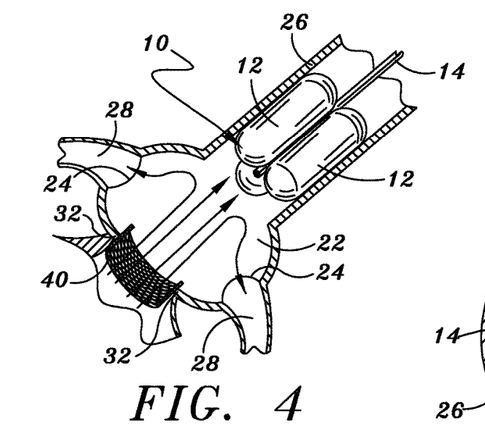
FIG. 4 illustrates the fluid dynamics of the deployed TAV system of the present invention positioned as in FIG. 2, during systole, with the native aortic valve ablated and ablation stent in place.

The native aortic valve 30 comprised of valve leaflets 31 is shown in FIG. 2. Substituted therefore in FIGS. 3 and 4 is an ablation stent 40, lodged within the aortic annulus 32, following ablation of native aortic valve 30 and leaflets 31. Ablation of the tissues of native valve 30 into the aortic annulus is an important step in the PAV implantation procedure further discussed below.

Once the native valve 30 tissues have been ablated as shown in FIGS. 3 and 4, acute wide-open AI occurs at the level of aortic annulus 32. Meanwhile, TAV 10 serves as a control valve for the amount of AI rushing back to left ventricle 34. Massive acute AI during systole is prevented, thereby maintaining patient stability, as further demonstrated by the Mathematical Considerations set forth below.

FIG. 4 illustrates the fluid dynamics of the method of the present invention with TAV 10 deployed during systole. The arrows depict partially obstructed blood flow through TAV 10 and unobstructed flow into coronary arteries 28. TAV 10 allows for temporary pressure build-up in the region of Sinus of Valsalva 22, enhancing partial systolic coronary perfusion. After native valve 30 (shown in FIG. 2) is ablated, the pressure gradient along the flow path is relocated from native valve 30 to TAV 10.

As demonstrated by the Mathematical Considerations set forth below, the AS at TAV 10 will be less than the critical value at the native aortic valve stenosis. Because TAV 10 is located above the level of coronary ostia 24, TAV 10 serves two major purposes. First, TAV 10 can enhance partially the systolic filling of coronary arteries 28. More importantly, after native aortic valve 30 (shown in FIG. 2) is ablated, eliminating the native aortic stenosis, the lower degree of AS offered by TAV 10 will immediately relieve the effective transvalvular pressure gradient as illustrated in FIG. 4. Lastly, because wide-open blood flow is prevented within the ascending aorta between left ventricle 34 (shown in FIG. 2) and TAV 10, the relative quiescent hemodynamic conditions, along with the open channel created by ablation stent 40 at the aortic annulus 32 (as depicted in FIGS. 3 and 4), allow for fine positioning, placement and deployment of the PAV within this region.

Mathematical Considerations of AI/AS at the Temporary Aortic Valve

Figure 5:
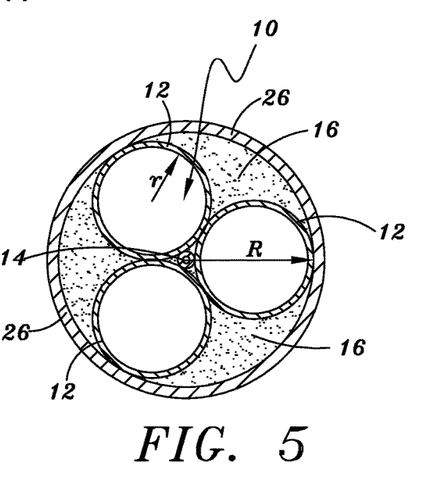
FIG. 5 shows the fully deployed TAV in cross section, taken along line 1-1 of FIG. 2, illustrating the radius of the TAV balloon components (assuming all balloons are of equal radius) relative to the radius of the ascending aorta, and gaps (shaded area) that permit continuous blood flow.

Referring to cross-sectional illustration FIGS. 1 and 5, the shaded areas represent gaps 16 between the inflated TAV balloons 12 and aortic wall 26. Gaps 16 also reflect the effective AI and AS, created during diastole and systole respectively, following inflation of TAV 10 against aortic wall 26.

Referring to FIG. 5, the calculation of the effective AI and AS at TAV 10 is as follows:

R=radius of ascending aorta 20 r=radius of a supporting balloons 12; all three balloons 12 according to the embodiment illustrated being of equal size and shape R~2.15r (by simple geometry), assuming adequate apposition of balloons 12 to aortic wall 26

Shaded area (gaps 16) for blood flow~35% of the cross-sectional area of ascending aorta 20

Well documented physiologic significant AI begins at >60% of the cross-sectional area of aortic annulus 32, as measurable by Doppler echocardiography in the parasternal short-axis view [Zobhbi W A, et al., *J Am Soc. Echocardiogr* 2003; 16:789]. Assuming application of TAV 10 positioned and deployed within ascending aorta 20 as shown, the calculated effective AI of 35% is categorized as moderate range in severity and should be well-tolerated by the patient even if it occurs acutely, e.g., after complete ablation of native aortic valve 30.

Clinically significant AS is considered when the aortic valve area (AVA) is reduced to below 25% of its original cross-sectional area [Carabello B, *N Engl J Med* 2002; 346(9):677-682]. For example, a normal adult aortic orifice area is approximately 3 $cm^2$, and a calculated AVA of less than 0.75 $cm^2$ is considered significant. The calculated effective AS of TAV 10 of 35% falls within the moderate range, and should be an improvement from the patient's original condition of critical native aortic stenosis and should be well-tolerated.

The amount of effective AI and AS created by TAV 10 during diastole and systole, respectively, may be altered by varying the numbers, size and/or shapes of supporting balloons means 12.

According to one preferred embodiment of the subject invention, TAV 10 is comprised of plurality of inflatable means 12 having a shape and size such that, when inflated and lodged against aortic wall 26, gaps 16 are created reflecting approximately 35% of the cross-sectional area of ascending aorta 20.

According to a further preferred embodiment of the subject invention, TAV 10 is comprised of plurality of inflatable means 12 having a shape and size such that, when inflated and lodged against aortic wall 26, gaps 16 are created reflecting between 0% and 60% of the cross-sectional area of ascending aorta 20.

According to a further preferred embodiment of the subject invention, TAV 10 is comprised of plurality of inflatable means 12 having a shape and size such that, when inflated and lodged against aortic wall 26, gaps 16 are created reflecting between 25% and 100% of the effective aortic valve area (AVA).

According to a further preferred embodiment of the subject invention, TAV 10 is comprised of plurality of inflatable means 12 having a shape and size such that, when inflated and lodged against aortic wall 26, gaps 16 are created reflecting between 25% and 60% of the effective aortic valve area (AVA).

According to a further preferred embodiment of the subject invention, TAV 10 is comprised of plurality of inflatable means 12 having a shape and size such that, when inflated and lodged against aortic wall 26, gaps 16 are created the total cross-sectional area which is at least 0.75 $cm^2$ in the case of an adult patient.

General Method of Replacement of the Native Aortic Valve with TAV in Place

Figure 6:
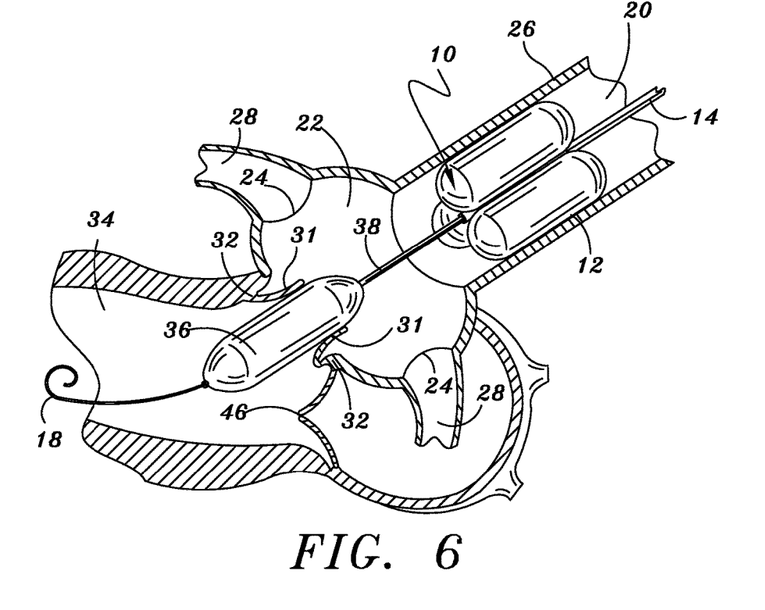
FIG. 6 shows the step of the percutaneous aortic valve (PAV) replacement procedure involving pre-dilation of the native aortic valve using a conventional valvuloplasty balloon in preparation for valve ablation.
Figure 7:
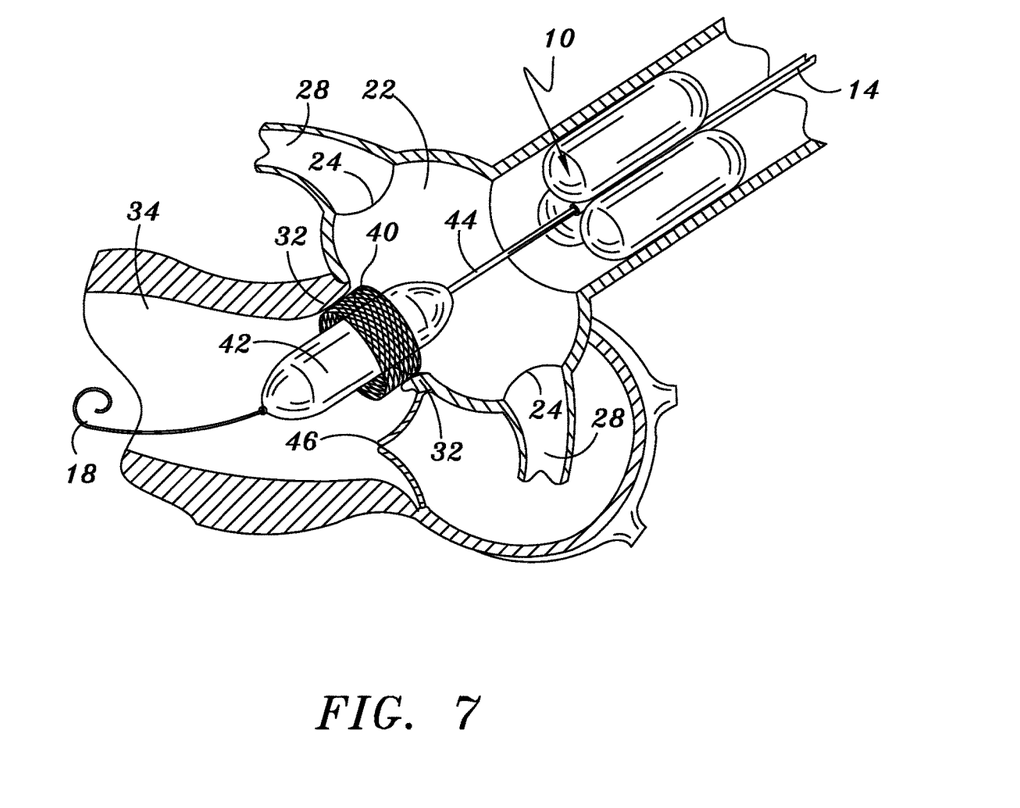
FIG. 7 illustrates the subsequent step of the PAV replacement procedure wherein the native aortic valve is entrapped and ablated against the aortic annulus using a balloon mounted ablation stent, preparing the aortic annulus to receive the PAV.
Figure 8:
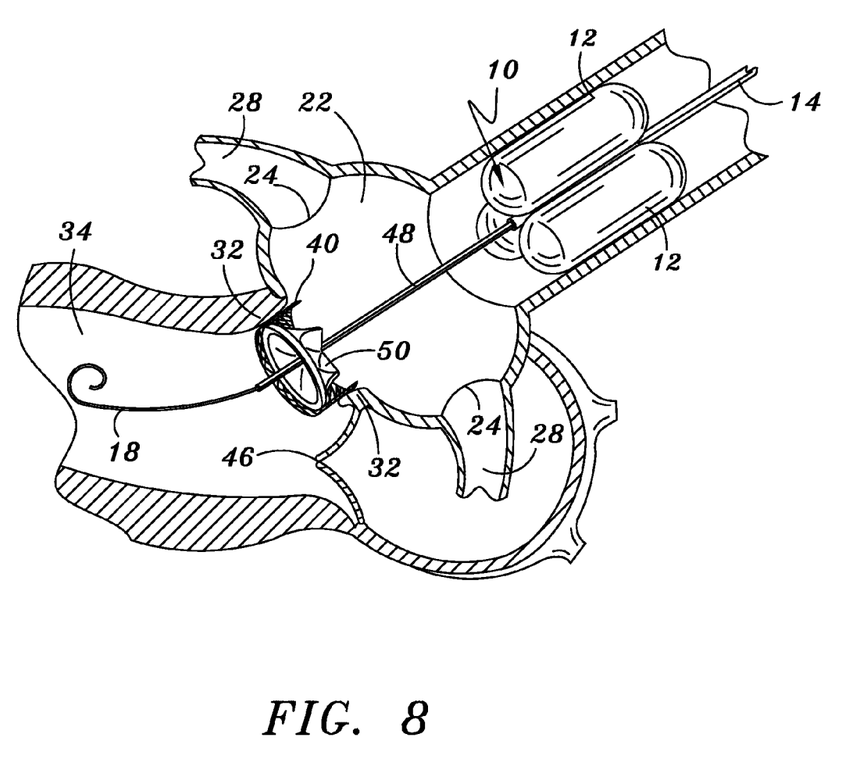
FIG. 8 illustrates the step of the PAV replacement procedure during which the PAV is delivered, positioned, and deployed at the site of the native aortic valve inside the ablation stent. The TAV remains inflated during PAV positioning and deployment, thereby moderating the hemodynamic forces, encouraging coronary perfusion, and reducing the pressure gradient experienced by the heart muscle. Like the low profile ablation stents, the PAV demonstrates a low profile relative to conventional PAVs with less metal, allowing for the use of a significantly reduced diameter central delivery catheter. The PAV is pressed up against the prepared aortic annulus and housed by the low profile ablation stent(s).

The general method of the subject invention is illustrated in FIGS. 6 through 8.

The materials and methods for the percutaneous introduction of catheters, stents, lumen and related surgical tools into the ascending aorta from the femoral artery are well known to those who practice in the field. The method of the subject invention assumes and incorporates by this reference all such familiar and conventionally employed materials and methods, together with the novel tools and devices more particularly described below and illustrated in the accompanying drawings.

Referring to FIG. 6, the procedure for implantation of a percutaneously delivered prosthetic aortic valve (PAV) begins with crossing native aortic valve 30 (as shown in FIG. 2) with a guide wire 18 in a retrograde fashion. TAV 10, in deflated mode, is advanced to position within ascending aorta 20 over guide wire 18 by means of central catheter 14. Supporting balloons 12 of TAV 10 are inflated to adequate apposition to aortic wall 26.

Once inflated, TAV 10 is operational, functioning as a temporary valve to facilitate the remainder of the PAV implantation procedure. As explained above, TAV 10 provides an environment of tolerable AI and AS following ablation of the native aortic valve and during positioning and placement of the bio-prosthetic replacement valve.

The remaining tools and devices for the valve replacement procedure are transported over guide wire 18 within central catheter 14, and within further particularized catheters or stents that are specific to the tool or device in question. The stable conduit provided by TAV 10, with balloons 12 fully inflated and lodged against aortic walls 26, facilitates the reliable transportation of these remaining PAV implantation tools and devices.

FIG. 6 also illustrates the step of pre-dilation of stenotic native aortic valve 30 in order to prepare valve 30 for ablation. A conventional valvuloplasty balloon 36 of the type commercially available [Bahl V K, et al., *Cathet Cardiovasc Diagn* 1998; 44(3):297-301], is built on a delivery catheter 38 and advanced over guide wire 18 through central catheter 14. Once in position across native aortic valve 30, balloon 36 is inflated, dilating native valve 30. Following valve 30 dilation, balloon 36 with catheter 38 is withdrawn.

Ablation of native aortic valve 30, the next step in the percutaneous valve replacement procedure, employs an aortic annulus stent 40. Ablation of native valve 30 with annulus stent 40 prior to PAV implantation greatly facilitates the precise and reliable positioning and placement of the PAV by providing an unobstructed path and platform for PAV implantation as compared with the conventional procedure, wherein the PAV is positioned and deployed in the presence of native aortic valve 30 with the valve leaflets 31 intact (as shown in FIG. 2).

As illustrated in FIG. 7, ablation stent 40 with a stent deployment balloon 42 is advanced to the site of native aortic valve 30 by means of a stent catheter 44 over guide wire 18 and through central catheter 14. Once in place, ablation stent 40 is deployed through inflation of deployment balloon 42, displacing and entrapping native valve 30 with leaflets 31 against aortic annulus 32. Ablation stent 40 with deployment balloon 42 functions in a manner analogous to coronary stents used in the treatment of atherosclerotic plaques. Ablation stent 40 remains permanently in position within aortic annulus 32 while deployment balloon 42 with stent catheter 44 is withdrawn.

The final step in the method of the subject invention, placement of a percutaneous aortic valve (PAV) 50, is illustrated in FIG. 8. Aortic annulus 32 has been optimized for PAV 50 placement by addressing two significant obstacles: diseased valve 30, removed through deployment of ablation stent 40 (FIG. 7), and the hemodynamic pressure gradient, relocated and minimized (as shown in FIGS. 3 and 4) through deployment of TAV 10.

PAV 50 with a deployment catheter 48 is advanced over guide wire 18 through central catheter 14 until in position within aortic annulus 32 and ablation stent 40. PAV 50 can now be ideally positioned clear of the mitral valve 46 and coronary ostia 24, and deployed by means of catheter 48 precisely, with minimal undue axial movements and relative ease.

Once PAV 50 has been deployed into position within ablation stent 40, which itself is lodged within aortic annulus 32, deployment catheter 48 and any remaining deployment tools can be withdrawn over guide wire 18 through central catheter 14. TAV 10 can then be deflated and withdrawn. Alternatively, TAV 10 can be left in position, temporarily, while the performance of PAV 50 is monitored during post-op and healing. Withdrawal of central catheter 14 and guide wire 18 completes the procedure.

Method of Replacement of the Native Aortic Valve Employing the Sequential Delivery of Low Profile PAV Components Preferred embodiments of the method of replacement of the native aortic valve with a bio-prosthetic valve within the aortic annulus, comprising the sequential delivery of low profile ablation stents and other PAV components, through a miniaturized delivery system, are illustrated in FIGS. 7 through 11.

Referring again to FIG. 7, ablation stent 40 is shown fully deployed within aortic annulus 32. Because TAV 10 allows the subject to experience a temporary stable cardiovascular hemodynamic condition when the native aortic valve is ablated and no longer functional, an immediate deployment of a functional PAV is not necessary. The surgeon has time to carefully prepare the aortic annulus to accept the PAV.

Furthermore, the support structure of the PAV does not have to serve as both the mechanical prop for the annulus' opening and the framework for the tissue valve. Ablation stent(s) 40 deployed within the aortic annulus can modify the local geometry toward a favorable housing to receive the PAV, and can assume most, if not all, of the mechanical load (radial force) to maintain the desired annulus lumen. The framework for PAV 50 itself can therefore be smaller and less bulky, serving only to structure the tissue valve. Miniaturization of the delivery system is, therefore, possible by focusing on the design strategies of the ablation stent system and the new PAV system.

Figure 7A:
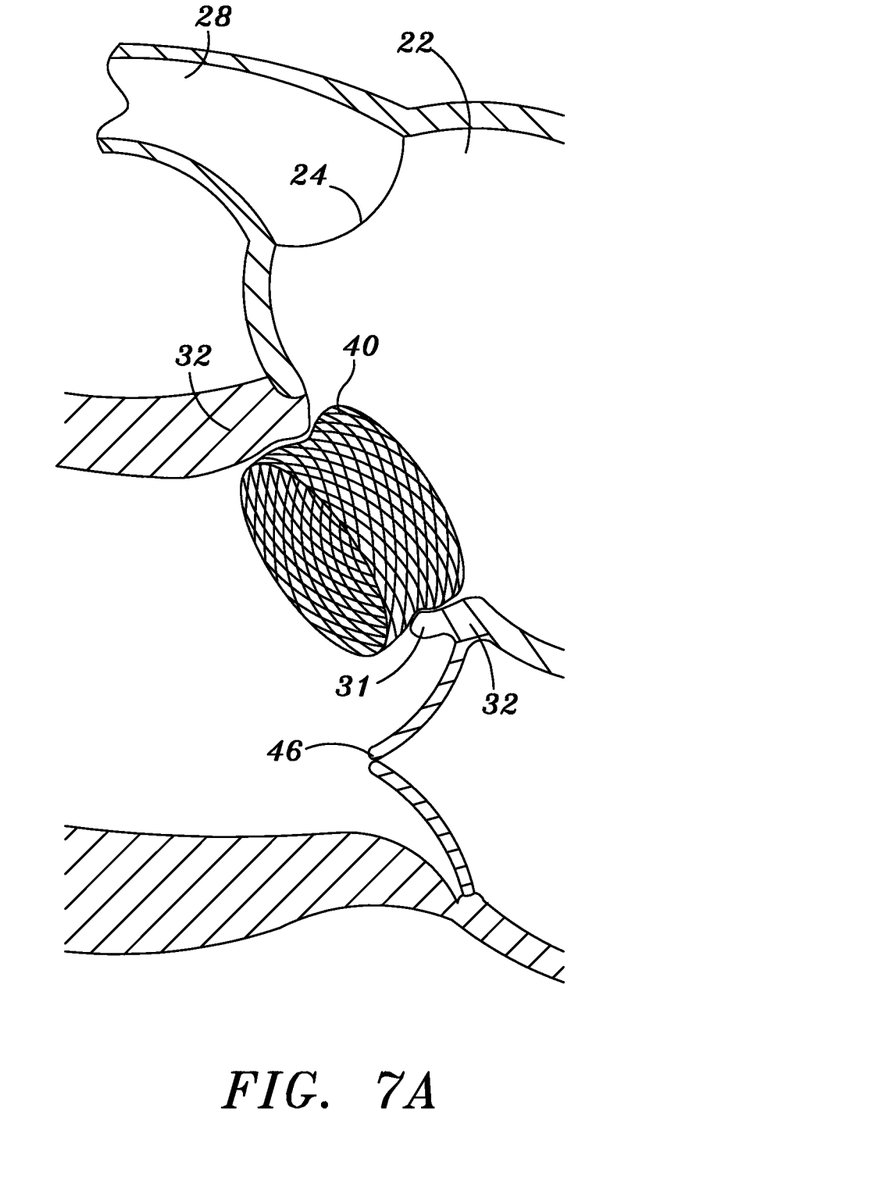
FIG. 7A illustrates the low-profile ablation stent of the subject invention, demonstrating a thinner design than conventional ablation stents, and allowing the use of a guiding catheter having a reduced diameter.
Figure 7B:
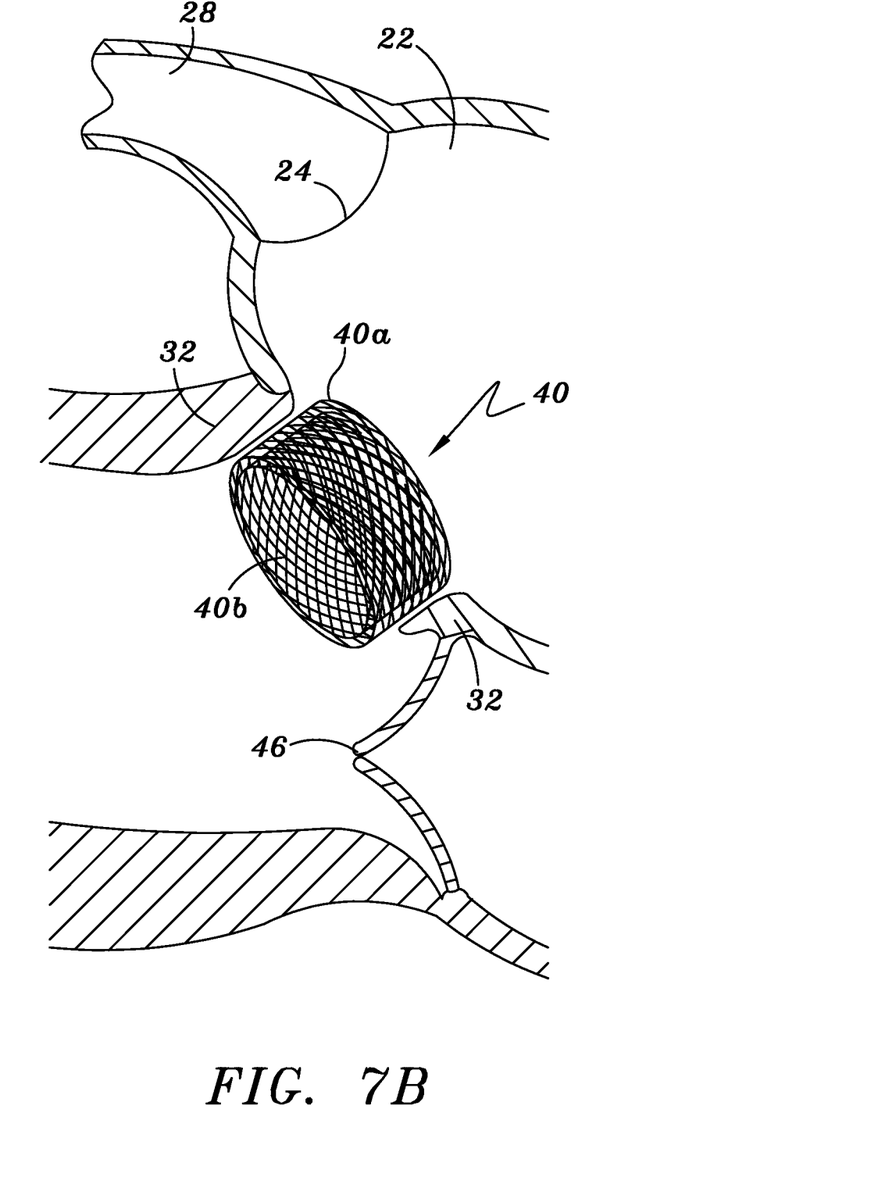
FIG. 7B shows a second low profile ablation stent inserted, concentrically, within a first low profile ablation stent, the two thin ablation stents together achieving adequate radial strength to prevent recoil of the native valve materials into the annulus lumen.

The novel low profile stent and PAV delivery system of preferred embodiments of the instant invention focus in two areas: and employment of deliberate shortening during stent 40 delivery and deployment (illustrated in FIGS. 9A and 9B); and the sequential delivery of thin ablation stents 40 (illustrated in FIGS. 7A and 7B).

Shown in FIG. 7A from the side is a first ablation stent 40a demonstrating a lower profile. Low profile ablation stent 40a is thinner, and contains less metal, than stents commonly employed in coronary procedures, allowing the use of a guiding catheter with reduced diameter. Ablation stent 40a is shown in FIG. 7A in deployed state, pressing outward against valve leaflets 31 and aortic annulus 32. Due to low profile stent 40a being thinner, and possessing less radial strength as compared with thicker stents, first deployed ablation stent 40a is shown in FIG. 7A as unable to fully push open leaflets 31 and annulus 32, leaving residual stenosis.

FIG. 7B illustrates, again in perspective, the use of sequentially deployed ablation stents 40 to fully ablate aortic annulus 32 to prepare annulus 32 for implantation of PAV 50. A second low profile ablation stent 40b, identical or substantially identical to first low profile ablation stent 40a, is shown deployed concentrically within first ablation stent 40a. The two thin ablation stents 40a and 40b, both now fully deployed, together achieve adequate radial strength to prevent recoil of the native valve aortic annulus 32 into the annulus lumen.

The use of multiple, concentrically placed, thin stents to achieve sufficient combined radial force to overcome resistant luminal narrowing has been shown efficacious in the context of colonic procedures. [yelling T E et al., *American Journal of Roentgenology* 2000; 175:119-120]. Although each thin stent 40 alone may possess inadequate radial strength to eliminate residual stenosis (FIG. 7A), the addition of multiple stents, concentrically positioned, can add to the overall amount of metal and radial support to achieve full luminal expansion (FIG. 7B). The advantage of using multiple thinner stents 40 is to allow for reduction in diameter of the delivery system, because each low profile stent 40 can be delivered using a smaller guiding catheter.

While FIG. 7B illustrates the use of a first 40a and second 40b ablation stent to maintain aortic annulus 32 in an adequately dilated state, preferred embodiments of the method the subject invention also contemplate the use of a single low profile ablation stent 40 of sufficient radial strength, or the use of three or more concentrically deployed low profile ablation stents 40, each demonstrating relatively less radial strength.

The choice of the stent material can further decrease the profile of valve ablation stents 40. Stents 40 can be fabricated from high strength composite materials, synthesized from combinations of metals, metal alloys and plastics for example, to provide low profile stents 40 capable of demonstrating significant radial strength.

Referring again to FIG. 8, PAV 50 is delivered, positioned, and deployed at the site of native aortic valve inside low profile ablation stent(s) 40. TAV balloons 12 remain inflated during PAV 50 positioning and deployment, thereby moderating the hemodynamic forces, encouraging coronary perfusion, and reducing the pressure gradient experienced by the heart muscle. Like low profile ablation stent(s) 40, PAV 50 demonstrates a low profile relative to conventional PAVs, with less metal. PAV 50 is pressed up against aortic annulus 32 earlier prepared (FIGS. 7A and 7B) through the deployment of low profile ablation stent(s) 40.

The delivery design of low profile ablation stent(s) 40 also help to reduce the size of delivery catheter 44 and, therefore, the overall diameter of the delivery system. The conventional coronary stent is intentionally designed to avoid significant amounts of foreshortening during deployment. Foreshortening is defined as a reduction in length of the stent in the expanded state. In percutaneous coronary intervention, foreshortening can lead to unpredictable stent location, and therefore considered an undesirable feature.

Figure 9A:
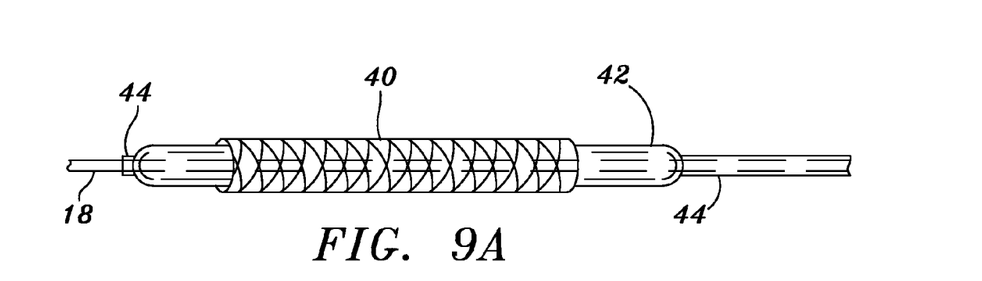
FIG. 9A shows the low profile stent design of the subject invention maximizing the axial distribution of metallic material while in the pre-deployment (crimped) state, delivered on a reduced diameter guiding catheter.
Figure 9B:
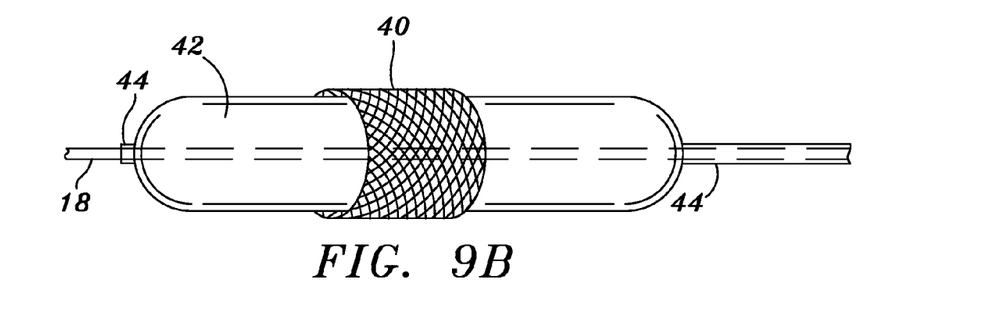
FIG. 9B illustrates the low profile stent, expanded and foreshortened at the aortic annulus by means of an inflated balloon, concentrating the metallic element at the annulus where maximal load-bearing is needed.

In the preferred embodiment PAV replacement procedure of the subject invention, the use of ablation stents demonstrating deliberate foreshortening upon deployment provide significant advantages. It allows for the axial (along the catheter length) distribution of metallic material in the crimped position, while the intended foreshortening can concentrate metallic support at the aortic annulus in the expanded state (FIGS. 9A and 9B). An anchoring or centering mechanism may be used to facilitate predictable stent location during deployment. The predictability of the stent location is also increased by the quiescent hemodynamics created by the TAV.

FIG. 9A illustrates low profile design ablation stent 40 of the subject invention in the pre-deployment (crimped) state, being delivered around deflated deployment balloon 42 and a reduced diameter stent delivery catheter 44, all travelling over guide wire 18. Low profile ablation stent 40 is shown stretched lengthwise, demonstrating deliberate foreshortening, further lowering the profile of the delivery system and maximizing the axial distribution of metallic material while in the pre-deployment (crimped) state.

FIG. 9B shows low profile stent 40 in deployed state, expanded and deliberately foreshortened at aortic annulus 32 (shown in FIG. 8) by means of inflated deployment balloon 42. Deployment of thin stent 40 concentrates the metallic element at annulus 32 where maximal load-bearing is needed.

Figure 10A:
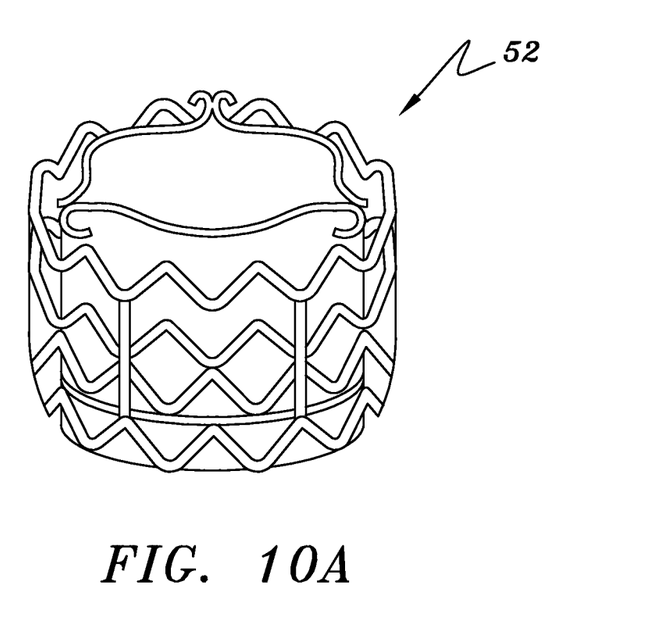
FIG. 10A shows an example of a conventional, prior art PAV, demonstrating a large and bulky metallic supporting frame.

With concentrically deployed ablation stent(s) 40 bearing most of the mechanical load to maintain the aortic annulus lumen and geometry, the new PAV can also be fashioned to a lower profile system. PAV 50 can be fabricated without the bulky stent structure as seen in current models (FIG. 10A). PAV 50 only requires a thin framework to support the tissue valve alone, and can be packaged and delivered in a significantly reduced French-size guiding catheter. With support from deployed TAV 10, and native aortic valve annulus 32 sufficiently prepared and dilated by low profile ablation stent(s) 40, the delivery and deployment of low profile PAV 50 can be precise and relatively uncomplicated.

Figure 10B:
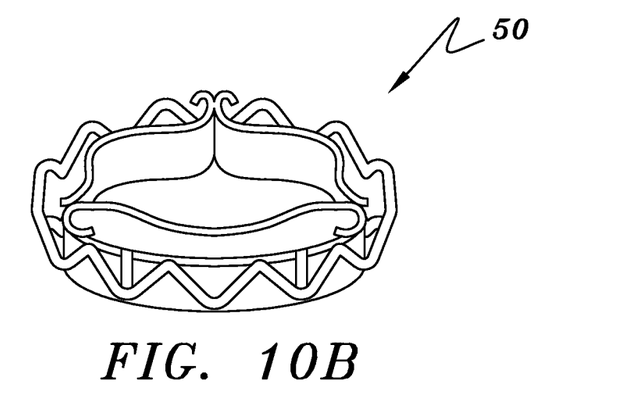
FIG. 10B illustrates the new PAV of the subject invention, demonstrating a much reduced framework structure design allowing for a much narrower, lower profile, delivery system.

FIGS. 10A and 10B highlight the differences between conventional PAVs and the miniaturized, low profile, PAV 50 of the subject invention. Shown in FIG. 10A in perspective is an example of a conventional PAV 52. Prior art PAV 52 demonstrates a large and bulky metallic supporting frame in contrast to low profile PAV 50 illustrated in FIG. 10B. The new PAV 50 of the subject invention exhibits a much reduced framework structure design. PAV 50 is framed using less supporting material or struts, and is more compact, compared with prior art PAV 52, allowing for a much smaller, lower profile, delivery system.

Due to use of low profile ablation stents 40 and PAV 50, and the ability to delivery stents 40 in elongated form, the entire delivery system of the method of the subject invention can be miniaturized. Typical French sizes of central guiding catheter mechanisms currently employed in PAV procedures are 21-24 French, with some thinner ones approaching 18 French. Referring to again FIG. 8, the slimmed down PAV components of the subject invention can be delivered to aortic annulus 32 through central catheter 14 having a French size of only 8-12.

At the completion of the procedure, TAV 10 is withdrawn along with guide wire 18. Manual removal of TAV 10 is possible when the activated clotting time is in standard range, similar to removal of an intra-aortic balloon pump.

Figure 11:
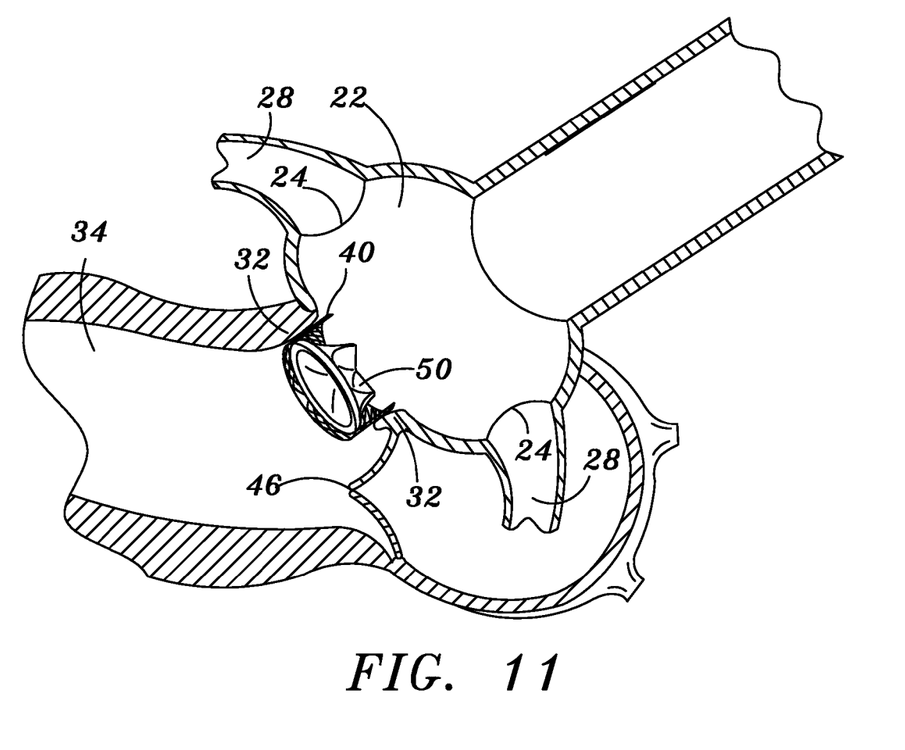
FIG. 11 shows the final result of the replaced bio-prosthetic aortic valve via the TAV-PAV technology of the subject invention.

The final outcome of the procedure, illustrated in FIG. 11 from the side, is a well-placed PAV 50 securely anchored inside an optimally-modified housing prepared and provided by ablation stent(s) 40 at the aortic annulus 32. The replacement valve is comprised of sequentially delivered low profile stent(s) 40 and PAV 50, together providing adequate radial strength to maintain aortic annulus 32 well dilated and a secure long-term housing for PAV 50.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SUMMARY AND SCOPE

The invention disclosed and described above presents an empirical design for a PAV replacement system offering a novel, viable and improved technology for the delivery and deployment of improved lower profile percutaneous aortic valves or valved stents.

The greatest pitfalls of the PAV replacement procedure are the close proximity of vital structures such as the mitral valve apparatus and the coronary ostia, the difficulty of correctly positioning the PAV device in an environment of high velocity flow and hemodynamic turbulence, the anatomic obstacle of the diseased native valve, and the bulky nature and large French size of conventional stents and PAV components.

The multi-balloon configured temporary aortic valve apparatus of the present invention relocates the highest pressure gradient downstream to the ascending aorta following ablation of the native valve. The multi-balloon TAV allows for a more quiescent hemodynamic environment at the aortic annulus level for PAV positioning, while providing adequate coronary perfusion during the cardiac cycle. Ablating the native aortic valve with an ablation stent removes the obstructive nature of the diseased valve structure, further facilitating the delicate placement of the PAV.

The central guiding catheter mechanism, with the multi-balloon TAV mounted at the tip, can be fashioned to the necessary French-size to accommodate the PAV device and related tools. The contiguous design of the TAV and the central guiding catheter provide added mechanical stability and support for the delivery and deployment of the predilatation balloon, the valve ablation stent, and the PAV device with deployment tools. Left ventricular trauma leading to cardiac tamponade from rigid guide wires have been reported as a significant source of periprocedural complication [Grube E et al., *J Am Coll Cardiol* 2007; 50:69-768]. The substantial mechanical support provided by the TAV-guiding catheter system decreases the need for a more aggressive and stiff guide wire for equipment transport and permits the use of novel, low profile, ablation stent(s) and PAV components.

Based on the TAV design, significant reduction in the diameter of the delivery catheter, with French size in the 8-12 range, is possible. The combination of the TAV hemodynamic support and the reduction in catheter size of the overall PAV system can finally bring this technology to mainstay therapy. The temporary and relatively stable hemodynamic conditions achieved by the TAV can afford time to prepare (to pre-treat) the aortic annulus. Strategies for pre-treatment of the annulus may include the use of balloon or debulking devices, and the use of the low profile ablation stent system to achieve an optimally circular and unobstructed housing for the PAV as described. Patients with the most difficult anatomy may be approached in this fashion. By utilizing multiple smaller profile ablation stents and minimizing the bulky frame of the PAV, the diameter of the delivery system can significantly be reduced. The patient can be left with a well-placed PAV in a secure housing with improved hemodynamics and only a band-aid at the femoral access site.

The valve ablation stent(s) are designed and constructed to have adequate radial strength, individually or used together, to entrap and hold the native diseased aortic valve tightly against the annulus. These stents may have drug-elution capability.

The disclosed PAV delivery and deployment system of the present invention, as with some current models, can also be used to replace the aortic valve in severe aortic insufficiency without stenosis. In isolated aortic insufficiency, pre-dilatation prior to placement of the ablation stent may or may not be necessary. Case selection in this group of patients, however, may occasionally be somewhat challenging depending on the degree of pre-existing left ventricular dysfunction.

Design limitations of the presented system may exclude its use in patients with ascending aortic aneurysm or severe aortic root dilatation, severe isolated aortic insufficiency with end-staged cardiomyopathy, and perhaps the excessively bulky calcified aortic valve. In the case of severe aortic insufficiency without stenosis and end-stage cardiomyopathy, the patient may not tolerate the required transient effective moderate-range aortic stenosis created by the TAV in the ascending aorta. In the case of the excessively calcified aortic valve, adequate entrapment and ablation of the native valve may be difficult; adequate lumen for PAV implantation may be compromised in this scenario.

While the present invention has been described in terms of specific structures, specific configurations of structures, and specific method steps, representing the currently understood preferred embodiments, the invention should not be conceived as limited to these specific structures, configurations or steps.

By way of example and not limitation, two or more than three balloons 12 may be substituted for the three balloons 12 comprising TAV 10 shown in FIGS. 1 through 8, and the size and shape of balloons 12 can be varied, absolutely or relative to one another. It should be clear to those schooled in the relevant art who consider this disclosure that the degree of AI and AS can be varied by varying the number, size and shape of balloons 12, as well as compliance of balloon 12 and its inflation pressure. Clinical circumstances may dictate different degrees of AI and AS for different patients, and patient aortic diameters differ. Optimal AI and AS for a given patient is achievable through the selection of number, size shape, compliance and associated inflation pressure of balloons 12.

Similarly, although the use of inflatable balloons in percutaneous circulatory procedures is well known and understood, alternative materials that can be alternatively expanded and compressed and that provide equivalent or superior functionality and utility to partially occlude the ascending aorta may be substituted for balloons 12 without departing from the spirit and scope of the subject invention.

As respect to concentrically deployed low profile ablation stent(s) 40 used to ablate the native valve and maintain open the annulus lumen, preferred embodiments of the method of the instant invention contemplate the use of one to three, or more than three, thin ablation stents 40 sequentially delivered and deployed. Low profile ablation stent(s) 40, and low profile PAV 50, may be delivered exhibiting different degrees of foreshortening, or no foreshortening; all such variations and alternatives being within the scope of the present invention.

The French size of central guiding catheter mechanism 14 can be varied, being as narrow as 6 French, as wide as 24 French, or anywhere in between. The stable support structure provide by the TAV and the low profile PAV components make possible the use of narrower central catheter mechanisms, but their use is at the surgeon's option.

Concerning the disclosed method, any of the various surgical tools and methodologies that have been disclosed or practiced in the fields of circulatory and cardiac medicine and, in particular, those tools and methodologies that are familiar to those who practice in the field of percutaneous cardiac procedures, may be substituted for the specific pre-dilation, ablation and PAV deployment tools, and the specific methodologies, described and depicted in the preferred embodiments disclosed herein, and all such substitutions and alternative tools and procedures being within the subject invention as contemplated. By way of example and not by way of limitation, the method of the subject invention involving ablation of the native valve in advance of PAV positioning and implantation may be used with some of the other disclosed steps omitted, or with steps not specifically disclosed herein substituted for certain disclosed steps, and with certain of the steps performed in a different order. By way of example, and not by way of limitation, the step of pre-dilation of the native aortic valve can precede the step of TAV deployment when indicated, as in the case of severe aortic valve stenosis. Similarly, the method of the subject invention may be used in conjunction with apparatus other than the TAV and PAV implantation tools specifically described above.

Accordingly, while the embodiments of the invention disclosed herein are presently considered to be preferred, various changes and modifications can be made without departing from the spirit and scope of the invention. The scope of the invention should be determined by the appended claims and their legal equivalents, rather than with reference to any particular example, embodiment or illustration.

What is claimed is:

1. A method for replacing a heart valve, having an annulus, with a low-profile prosthetic valve, the method comprising:
   deploying a temporary valve (TV) in a vessel in proximity to the annulus to partially occlude the vessel, the TV comprising a central catheter mechanism and an expandable occluding element surrounding a distal end of the central catheter mechanism;

deploying a plurality of low-profile stents within the valve annulus to prepare the annulus for implantation of the low-profile prosthetic valve, wherein the plurality of low-profile stents are advanced through the central catheter mechanism prior to deployment; and deploying the low-profile prosthetic valve inside the plurality of low-profile stents, wherein the low-profile prosthetic valve is advanced through the central catheter mechanism prior to deployment.

2. The method of claim 1, further comprising anchoring the low-profile prosthetic valve inside the plurality of low-profile stents.

3. The method of claim 1, wherein deploying the plurality of low-profile stents further comprises sequentially delivering the plurality low-profile stents.

4. The method of claim 3, wherein sequentially delivering the plurality of low-profile stents further comprises deploying the plurality of low-profile stents concentrically one within the other, wherein the prosthetic valve is housed within the plurality of low-profile stents.

5. The method of claim 1, wherein the heart valve includes a plurality of leaflets and wherein each of the plurality of low-profile stents has a radial strength insufficient to fully open the plurality of leaflets and the plurality of low-profile stents deployed within the valve annulus together has a total radial strength sufficient to fully open the plurality of leaflets and prevent recoil of the annulus and the plurality of leaflets of the valve.

6. The method of claim 1, wherein the plurality of low-profile stents has a plurality of radial strengths.

7. The method of claim 1, wherein the plurality of low-profile stents has a plurality of profiles.

8. The method of claim 1, wherein at least one stent of the plurality of low-profile stents is configured to have an elongated shape during delivery and a foreshortened shape after deployment.

9. The method of claim 1, wherein at least one stent of the plurality of low-profile stents comprises an ablation stent.

10. The method of claim 1, wherein at least one stent of the plurality of low-profile stents is fabricated from a high strength composite material.

11. The method of claim 1, wherein at least one stent of the plurality of low-profile stents has drug elution capabilities.

12. The method of claim 1, wherein delivering the plurality of low-profile stents comprises delivering at least one stent of the plurality of low-profile stents through the central catheter mechanism.

13. The method of claim 12, wherein the central catheter mechanism has a diameter less than 18 French.

14. The method of claim 13, wherein the central catheter mechanism has a diameter of not more than 8 French.

15. The method of claim 13, wherein the central catheter mechanism has a diameter of not more than 12 French.

16. The method of claim 1, wherein the TV is fabricated from a high strength composite material.

17. The method of claim 1, wherein the heart valve comprises an aortic valve.

18. The method of claim 17, wherein the TV comprises a temporary aortic valve (TAV) and the vessel is in an aorta, and wherein deploying the temporary valve (TV) comprises deploying the TAV above and in proximity to a Sinus of Valsalva of the aorta.

19. The method of claim 1, wherein the expandable occluding element comprises an inflatable balloon, and wherein deploying the temporary valve (TV) comprises inflating the inflatable balloon in proximity to the annulus.

20. The method of claim 1, wherein the expandable occluding element comprises a plurality of expandable occlusion elements.

21. The method of claim 20, wherein the plurality of expandable occlusion elements are distributed around the central delivery catheter.

22. The method of claim 20, wherein the plurality of expandable occlusion elements comprise three occlusion elements of equal size, and wherein deploying the temporary valve comprises arranging the three occlusion elements to provide gaps therebetween to allow continuous blood perfusion.

23. The method of claim 20, wherein the plurality of expandable occlusion elements comprises three occlusion elements of unequal size, and wherein deploying the temporary valve comprises arranging the three occlusion elements to provide gaps therebetween to allow continuous blood perfusion.

* * * * *